United States Patent [19]

Rudolph et al.

[11] 4,382,041

[45] May 3, 1983

[54] PROCESS FOR THE PRODUCTION OF AROMATIC CARBOXYLIC ACID CHLORIDES

[75] Inventors: Udo Rudolph; Manfred Schmidt; Dieter Freitag; Ludwig Bottenbruch, all of Krefeld, Fed. Rep. of Germany

[73] Assignee: Bayer Aktiengesellschaft, Leverkusen, Fed. Rep. of Germany

[21] Appl. No.: 312,223

[22] Filed: Oct. 19, 1981

[30] Foreign Application Priority Data

Oct. 25, 1980 [DE] Fed. Rep. of Germany ........ 3040294

[51] Int. Cl.³ ............................................. C07C 51/60
[52] U.S. Cl. ............................ 260/544 D; 260/544 B; 260/544 P
[58] Field of Search ............ 260/544 D, 544 B, 544 P

[56] References Cited

FOREIGN PATENT DOCUMENTS 2841069 4/1976 Fed. Rep. of Germany .

OTHER PUBLICATIONS

Patai, Saul, "The Chemistry of Acyk Halides", (1972), p. 36, Interscience, Publ.

*Primary Examiner*—Natalie Trousof
*Assistant Examiner*—L. Hendriksen
*Attorney, Agent, or Firm*—Connolly and Hutz

[57] ABSTRACT

A single-stage process for the production of pure aromatic carboxylic acid chlorides by reacting an aromatic carboxylic acid or an aromatic carboxylic acid mixture with thionylchloride in the presence of tert. phosphine as the catalyst.

3 Claims, No Drawings

PROCESS FOR THE PRODUCTION OF AROMATIC CARBOXYLIC ACID CHLORIDES

This invention relates to a single stage process for the production of extremely pure, polycondensable, aromatic carboxylic acid chlorides.

The reaction of aliphatic and aromatic carboxylic acids with thionyl chloride is a standard process of organic chemistry for the production of the corresponding acid chlorides. However, during this process, dark-coloured carboxylic acid chlorides are obtained as the reaction products with a purity of from 96 to 99%. Aromatic dicarboxylic acid dichlorides of this low purity level cannot be directly used for the production of high-molecular-weight polycondensates, such as aromatic polyamides or aromatic polyesters according to the two-phase interface polycondensation process. A purity of at least 99.6% is necessary for this purpose. Their content of unreacted or only unilaterally reacted dicarboxylic acids disturbs the polycondensation process, causes an undesirable chain termination and produces polymers having terminal carboxyl groups. The aromatic dicarboxylic acid dichlorides thus produced are dark in colour due to impurities and in addition thereto, they contain sulphur in elementary and bound form which further impairs the characteristics of the polycondensates to be produced.

During the production of acid chlorides using thionyl chloride and dimethylformamide as catalyst (see German Pat. No. 1,026,750), considerably quantities of dimethylcarbamic acid chloride may be produced as the by-product which contaminate the product or accumulate in the excess thionyl chloride which is possibly reduced.

In order to obtain colourless carboxylic acid chlorides, the crude products have to be purified by recrystallisation or distillation. These measures necessitate additional expense and reduce the yield; moreover a risk of spontaneous decomposition exists with distillation.

The object of the present invention is a one-stage process for the production of pure aromatic carboxylic acid chlorides by reacting aromatic carboxylic acids with thionyl chloride, which process is characterised in that tert. phosphines or the reaction products thereof with thionyl chloride and/or with the acid chlorides to be produced are used as catalysts. The aromatic carboxylic acid chlorides thus obtained are substantially colourless and as well as containing the catalysts used, they also have a maximum content of 0.1% of impurities, so that they may be used without subsequent purification for the production of colourless, high-molecular-weight polycondensate.

The tert.phosphines used as catalysts according to the invention may in some cases be simply removed from the reaction mixture by distilling the reaction mixture after the reaction has finished, but remaining particles of the catalyst in the resulting carboxylic acid chloride do not disturb the conversion of, for example, dicarboxylic acid dichlorides into aromatic polyesters according to the process of the two-phase interface reaction.

Tert.phosphines of the following general structure (I) are suitable as catalysts which are active according to the invention:

wherein
R$_1$, R$_2$ and R$_3$ may be the same or different and represent
C$_1$-C$_8$-alkyl, C$_6$-C$_{10}$-aryl, C$_7$-C$_{20}$-alkylaryl or arylalkyl groups. They are preferably C$_6$-C$_{10}$-aryl radicals, such as phenyl or phenyl substituted with one or more C$_1$-C$_4$-alkyl radicals.

The following, for example, are mentioned as suitable catalysts: Tribenzyl phosphine, Triisopropyl phosphine, tributyl phosphine and triphenyl phosphine.

According to the invention, from 0.1 to 5.0% by weight, preferably from 0.2 to 3% by weight, based on the aromatic carboxylic acids, of tert. phosphines of the general structure (I) are used.

In principle, all aromatic carboxylic acids may be used. They correspond in particular to the following formulae (II) to (VII):

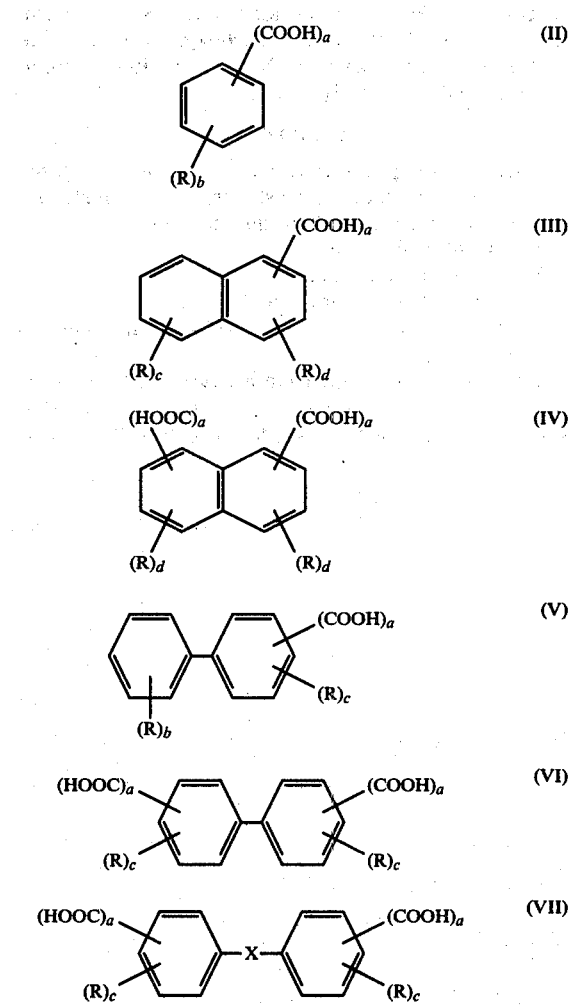

wherein
R represents a substituent selected from the group of alkyl groups having from 1 to 6 carbon atoms, halogen-substituted alkyl groups having from 1 to 6 carbon atoms, alkoxy groups, halogen-substituted alkoxy groups having from 1 to 6 carbon atoms and halogen atoms;

X represents an oxygen atom, a methylene group or an isopropylene group, a $C_5$-$C_7$-cycloalkylene radical or a —C═O—group;

a represents an integer from 1 to 3;

b represents an integer from 0 to 5;

c represents an integer from 0 to 4; and d represents an integer from 0 to 3.

The following are mentioned by way of example: phthalic acid, isophthalic acid, terephthalic acid, mixtures of iso- and terephthalic acid, 4,4'-dicarboxybenzophenone, diphenic acid, 1,4-naphthalene dicarboxylic acid and trimesic acid.

In order to carry out the process according to the invention, the aromatic carboxylic acids may be mixed with from 1 to 2 mols of thionyl chloride per carboxyl group after adding the catalysts according to the invention and this suspension or solution may be heated to a temperature of from 50° to 150° C., preferably from 80° to 100° C.

After distilling off the excess thionyl chloride and after applying a vacuum for a short time at the desired reaction temperature, a residue is obtained which consists to ≧ 99.9% of aromatic carboxylic acid chloride.

It is possible to carry out the process either continuously or discontinuously.

EXAMPLE

The following are introduced into a liter three-necked flask provided with a stirrer, a thermometer and a reflux cooler, and they are then heated:

83 g isophthalic acid;
83 g of terephthalic acid;
357 g of thionyl chloride; and
2 g of triphenyl phosphine (1.2% by weight, based on the acids).

The pale yellow suspension is heated to from 60° C. to 70° C. within 30 minutes, and a rapid evolution of HCl and $SO_2$ occurs. The gas evolution ceases after approximately 6 hours and a light-yellow solution is present, from which the excess thionyl chloride is removed at normal pressure and then under vacuum.

In addition to the catalyst, the residue contains the following:

≧ 99.9% of acid chlorides,
≦ 0.05% of COOH,
≦ 0.01% of S, and
≦ 0.05% of Cl.⁻

Aromatic polyesters with the following:

(a) η rel=1.54 (2 mol % chain terminator) and
(b) η rel=1.27 (5 mol % of chain terminator) were produced according to the conventional interface polycondensation process with this acid chloride mixture and bisphenol A, in the presence of o-phenylphenol as the chain terminator.

We claim:

1. In the process of producing an aromatic carboxylic acid chloride by reacting an aromatic carboxylic acid with thionyl chloride, the improvement wherein said reaction is carried out in the presence of a catalytic amount of tertiary phosphine.

2. The process of claim 1 wherein said tertiary phosphine catalyst is of the formula

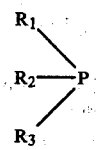

wherein $R_1$, $R_2$ and $R_3$ are the same of different and are selected from the group consisting of $C_1$-$C_8$-alkyl, $C_6$-$C_{10}$-aryl, $C_7$-$C_{20}$-alkaryl and $C_7$-$C_{20}$-aralkyl.

3. The process of claim 2 wherein $R_1$, $R_2$ and $R_3$ are the same or different and are selected from the group consisting of phenyl and phenyl substituted with one or more $C_1$-$C_4$-alkyl groups.

* * * * *